US005872359A

United States Patent [19]
Stewart et al.

[11] Patent Number: 5,872,359
[45] Date of Patent: Feb. 16, 1999

[54] REAL-TIME MONITOR AND CONTROL SYSTEM AND METHOD FOR HYDROGEN PEROXIDE VAPOR DECONTAMINATION

[75] Inventors: Bonnie Stewart, Durham; George Sparber, Broadway; Peter Zell, Raleigh, all of N.C.

[73] Assignee: American Sterilizer Company, Mentor, Ohio

[21] Appl. No.: 508,314

[22] Filed: Jul. 27, 1995

[51] Int. Cl.⁶ .......................... G01N 21/25; G01N 21/35
[52] U.S. Cl. ................................ 250/339.12; 250/339.09
[58] Field of Search ............................. 422/1, 3, 28, 32, 422/34, 108, 110, 111, 119, 62, 83, 91; 250/339.13, 339.12, 339.09, 343, 373

[56] References Cited

U.S. PATENT DOCUMENTS

| | | | |
|---|---|---|---|
| Re. 33,007 | 8/1989 | Bier | 203/12 |
| 2,617,940 | 11/1952 | Giguere. | |
| 3,569,696 | 3/1971 | Karlson. | |
| 4,323,777 | 4/1982 | Baskins et al. | 250/339.13 X |
| 4,641,973 | 2/1987 | Nestler et al. | 250/339.13 X |
| 4,661,320 | 4/1987 | Ito | 424/86 |
| 4,664,522 | 5/1987 | LeFebre | 356/328 |
| 4,680,271 | 7/1987 | Williams | 436/55 |
| 4,786,171 | 11/1988 | LeFebre et al. | 356/326 |
| 4,843,867 | 7/1989 | Cummings | 73/23 |
| 4,909,999 | 3/1990 | Cummings | 422/298 |
| 4,916,058 | 4/1990 | Aoyama | 435/10 |
| 4,956,145 | 9/1990 | Cummings | 422/28 |
| 4,998,018 | 3/1991 | Kurahashi et al. | 250/339.13 X |
| 5,055,690 | 10/1991 | Bonne | 250/339.13 X |
| 5,081,045 | 1/1992 | McGill | 436/135 |

(List continued on next page.)

FOREIGN PATENT DOCUMENTS

| | | | |
|---|---|---|---|
| 62-79331 | 4/1987 | Japan | 250/373 |
| 2262338 | 6/1993 | United Kingdom | 250/338.5 |

OTHER PUBLICATIONS

Shen, Ji et al., 1988. Development of Techniques for Measurement of Gas–Phase Hydrogen Peroxide. Brookhaven National Laboratory Associated Universities, Inc., pp. 1–47.
Kleindienst, T.E., et al., 1988. Comparison of Techniques for Measurement of Ambient Levels of Hydrogen Peroxide. Environ. Sci. Technol. 22:53–61.
Standard Practices for Sampling Atmospheres for Analysis of Gases and Vapors. ASTM Standard Designation D–1605–60 (Reapproved 1990), pp. 13–26.
Miller, Keith L. 1992. Fiber–Optic Spectroscopy: A New View of Your Process. PI Quality.
Lee, J.H. et al., 1993. Measurement and Speciation of Gas Phase Peroxides in the Atmosphere. Journal of Geophysical Research 98: 2911–2915.

(List continued on next page.)

*Primary Examiner*—Edward J. Glick
*Attorney, Agent, or Firm*—Fay, Sharpe, Beall, Fagan, Minnich & McKee

[57] ABSTRACT

The invention includes a system and a method for maintaining a selected concentration of a sterilant vapor during vapor phase sterilization. The system includes a sterilization chamber with a source of multicomponent vapor containing a sterilant vapor, an electromagnetic radiation source capable of generating radiation at a plurality of wavelengths, a radiation detector for detecting and quantitating the electromagnetic radiation absorbed at the wavelengths, the detector generating absorbance signals proportional to the concentration of the sterilant vapor in the multicomponent vapor, a microprocessor programmed to compare the absorbance signals with reference absorbance signals, to calculate the sterilant vapor concentration therefrom and to generate an output signal, and a controller to receive the output signal and to control addition of the sterilant vapor to the sterilization chamber to maintain a selected concentration of the sterilant vapor in the sterilization chamber during the sterilization process. The method allows sterilization conditions to be optimized to reduce the time required for and to increase the sterilization efficacy of the sterilization procedure.

25 Claims, 5 Drawing Sheets

U.S. PATENT DOCUMENTS

| | | |
|---|---|---|
| 5,139,956 | 8/1992 | Shick ........................................ 436/52 |
| 5,139,957 | 8/1992 | Grack ....................................... 436/135 |
| 5,167,927 | 12/1992 | Karlson ..................................... 422/90 |
| 5,173,258 | 12/1992 | Childers .................................... 422/27 |
| 5,184,193 | 2/1993 | LeFebre ................................... 356/325 |
| 5,339,155 | 8/1994 | Partridge et al. .............. 250/339.13 X |
| 5,384,640 | 1/1995 | Wong ............................ 250/339.13 X |
| 5,418,366 | 5/1995 | Rubin et al. ................... 250/339.13 X |
| 5,445,792 | 8/1995 | Rickloff et al. ........................... 422/28 |
| 5,475,222 | 12/1995 | King ................................ 250/338.5 X |
| 5,600,142 | 2/1997 | Van Den Berg et al. . |

OTHER PUBLICATIONS

Schneider, Philip M. 1994. Low–temperature sterilization alternatives in the 1990s. Tappi Journal 77(1): 115–119.

Kok, Gregory L. et al., A Brief Survey of Methods for the Measurement of Gas–Phase Hydrogen Peroxide. (Publication and date unknown).

UOP Guided Wave product literature: "For a New View of Your Process"; Fiber Optic Process Monitor Purchase Considerations; and Light Dispersing Technologies. Dates unknown.

UOP Guided Wave product literature: Process Monitoring Probes—"In–Situ Installation in Process Pipes or Reactors; Gas, Vapor and Liquid Measurements; Assemblies for Users to Construct Probes; NIR/VIS Double Beam Operation; Optical Transmission and Absorbance Measurement". Insite Laboratory Spectrophotometers. Fiber Optic Spectrophotometers for Remote NIR–VIS–UV Analysis. Dates unknown.

"The Infra–Red Spectrum of Hydrogen Peroxide", Giguère, et al., The Journal of Chemical Physics, vol. 18, No. 1, Jan. 1950.

REAL-TIME MONITOR AND CONTROL SYSTEM AND METHOD FOR HYDROGEN PEROXIDE VAPOR DECONTAMINATION

FIELD OF THE INVENTION

The present invention relates generally to a system and method of vapor-phase decontamination, and more particularly to a micro-processor controlled system and method of decontamination using a two-component vapor phase sterilant.

BACKGROUND OF THE INVENTION

Reusable medical instruments and pharmaceutical and biological equipment are generally sterilized before each use. Additionally, reusable containers employed in medical, pharmaceutical, and biological applications, such as gloveboxes and incubators, are generally sterilized before each use. Containers such as cassettes are employed first for sterilizing articles and then for maintaining the sterility of articles during post-sterilization storage. In facilities and applications where these types of instruments and containers are used several times a day, it is important to achieve sterilization efficiently and economically.

Several different methods have been developed for delivering a vapor phase sterilant to an enclosure or chamber for sterilizing the load (e.g., medical instruments or other articles) or interior thereof. In one option, the "deep vacuum" approach, a deep vacuum is used to pull liquid sterilant into a heated vaporizer; once vaporized, the sterilant vapor is drawn into an evacuated and sealed chamber. In another option, the "flow-through" approach, vaporized sterilant is mixed with a flow of carrier gas that serves to deliver the sterilant vapor into, through and out of the chamber, which may be at slightly negative or positive pressure.

Bier, U.S. Pat. No. Re. 33,007, Aug. 1, 1989, incorporated herein by reference, discloses a method of vaporizing a multicomponent liquid, such as hydrogen peroxide and water, and passing the vapor in successive small increments into a sterilization chamber.

Methods have been developed for optimizing vapor phase sterilization in a deep vacuum and/or flow-through system. Cummings, et al., U.S. Pat. No. 4,956,145, Sep. 11, 1990, incorporated herein by reference, discloses a deep vacuum method of vapor phase sterilization in which a predetermined concentration of hydrogen peroxide sterilant vapor is maintained in an evacuated, sealed chamber. The amount of liquid sterilant injected into a vaporizer is regulated or adjusted to account for the estimated decomposition of hydrogen peroxide sterilant vapor into water and oxygen in the closed system over time. In a different approach, a predetermined percent saturation is maintained in an open, flow-through sterilization system as disclosed in commonly assigned, copending application U.S. Ser. No. 08/237,406, entitled "Optimum Hydrogen Peroxide Vapor Sterilization Method," filed on May 2, 1994, and now U.S. Pat. No. 5,445,792 issued Aug. 29, 1995, incorporated herein by reference. This patent discloses regulation or adjustment of the rate of hydrogen peroxide vapor injection into a carrier gas in response to predetermined characteristics of the carrier gas.

Also, several systems and apparatus have been developed for conducting vapor phase sterilization. An open flow-through system designed to handle the disposition of residual sterilant vapors is disclosed in Cummings, et al., U.S. Pat. No. 4,909,999, Mar. 20, 1990, incorporated herein by reference. That system can be integrally associated with or releasably connected to a sealable container.

Childers, U.S. Pat. No. 5,173,258, Dec. 22, 1992, incorporated herein by reference, discloses another flow-through system in which vapor phase hydrogen peroxide is introduced into a recirculating, closed-loop flow of carrier gas. The hydrogen peroxide vapor is introduced and maintained at a predetermined concentration selected to optimize the sterilization cycle. The system includes a dryer to dehumidify the recirculating flow, preferably to at least about 10% relative humidity, and thereby prevent moisture build-up resulting from the decomposition of hydrogen peroxide vapor over time. By eliminating moisture build-up, the system can maintain the sterilization chamber at higher concentrations of vapor phase hydrogen peroxide sterilant for longer periods of time (i.e., the predried gas will accept more of the sterilant vapor). Further, to avoid condensation of the sterilant, the relative humidity in the chamber is preferably reduced (e.g., to at least about 10%) prior to introducing the sterilant vapor. After decontamination is complete, the enclosure may be rehumidified or conditioned if desired for the selected application.

Gas sterilization/decontamination systems rely on maintaining certain process parameters in order to achieve a target sterility or decontamination assurance level. For hydrogen peroxide gas sterilization/decontamination systems, those parameters include the concentration of the hydrogen peroxide vapor. By maintaining a sufficient concentration of hydrogen peroxide vapor and/or percent saturation at various temperatures and pressures for a sufficient period of time, desired sterility assurance levels can be successfully obtained while avoiding condensation due to vapor saturation. Existing systems typically monitor the amount of liquid delivered to the vaporization system over time, and, based on temperature, pressure, volume, and (where applicable) flow rate, calculate the theoretical concentration of hydrogen peroxide vapor, and then correlate some or all of these parameters with empirically derived estimates of hydrogen peroxide decomposition, to arrive at an estimate of the amount of hydrogen peroxide to inject into the system in order to maintain a sought theoretical concentration of hydrogen peroxide vapor. The sterilization performance is then validated empirically via microbiological efficacy testing.

Cummings, U.S. Pat. No. 4,843,867, Jul. 4, 1989, incorporated herein by reference, discloses a system for monitoring and controlling the concentration of one or more selected components in a multicomponent vapor, by measuring a property of the multicomponent vapor, such as dew point, measuring another property of the one or more selected components of the multicomponent vapor, such as relative humidity, and fitting the measured values for these properties into a model, thereby obtaining an estimate of the concentration of the selected component. The estimated concentration of the selected component allows Cummings to more closely control input of that component and thereby obtain a greater measure of control over its concentration in the sterilization chamber than was previously available. Cummings' method is an indirect approximation based on a number of empirical assumptions, including the estimated rate of loss of the component from the multicomponent vapor.

In actual practice several factors can affect the concentration of components of the vapor, such as decomposition, absorption and adsorption, all due to contact of the gas with various surfaces in the system, and dilution due to evaporation by water vapor from the loads being processed and to decomposition of the sterilant. These effects can vary from load to load and system to system. The need exists to adjust the supply of sterilant vapor to take these effects into account with a precise, real-time measure of the concentration of the sterilant vapor component of the multicomponent vapor in the sterilization chamber.

The foregoing methods and systems are effective at sterilization and/or provide an enhanced sterilization cycle. There exists, however, a need for further improvement in the measurement and control of the concentration of hydrogen peroxide vapor in the sterilization chamber.

SUMMARY OF THE INVENTION

The method of the present invention can be used to optimize the efficacy of vapor phase decontamination in either a flow-through cycle or in a deep vacuum cycle, or in a combination of the two cycles. The term "decontamination" shall be understood to include sterilization, disinfection, and sanitization. For the purpose of describing the preferred embodiments herein the objective discussed will be sterilization, as that term is understood by those skilled in the art. Although the terms "decontamination" and "sterilization" may be used interchangeably in this specification, it will be understood that the system and method of the present invention are applicable to all levels of biological contamination control, whether referred to as sterilization, decontamination, disinfection, or otherwise. The agent of decontamination may be referred to as the "sterilant" or the "sterilant vapor." The instruments, containers, equipment, and other items to be sterilized may be generally referred to as articles.

The present invention provides an optimized system and method for monitoring and controlling the concentration of hydrogen peroxide vapor in a sterilization chamber by employing direct, real-time measurement and control of the vapor concentration during the sterilization process.

The system directly measures absorption of electromagnetic energy by the hydrogen peroxide vapor present in the various portions of the sterilization chamber during the sterilization process, i.e., during real-time, thereby allowing control of the concentration of the vapor.

In addition to monitoring and controlling the concentration of hydrogen peroxide vapor, the system of the present invention may also monitor and control other portions of the overall operation of the sterilization system. The system may be conveniently viewed as comprising a monitoring subsystem and a process control subsystem. The present invention further provides a method of monitoring and controlling the concentration of hydrogen peroxide vapor in a sterilization chamber.

Preferably, the invention includes a system for maintaining a selected concentration of a sterilant vapor in one or more portions of the sterilization chamber during vapor phase sterilization. The system includes a sterilization chamber fluidly connected to a source of a multicomponent vapor, and the multicomponent vapor contains a concentration of sterilant vapor. The system further includes a radiation source for providing electromagnetic radiation at a plurality of wavelengths, the wavelengths preferably in the infrared region. The radiation at one of these wavelengths is absorbed by the sterilant vapor, and the radiation at a second of these wavelengths is absorbed by another vapor of the multicomponent vapor. Further, the system includes a radiation detector for detecting and quantitating the electromagnetic radiation at the first and second wavelengths. The detector generates at least first and second absorbance signals at the first and second wavelengths, the first absorbance signal having a strength at least partially proportional to the concentration of the sterilant vapor and the second absorbance signal having a strength proportional to the concentration of the other vapor in the multicomponent vapor but not to the sterilant vapor. The system further includes a microprocessor adapted to receive the absorbance signals, and programmed to compare at least the first and second absorbance signals with absorbance signals generated for known concentrations of the sterilant vapor and the other vapor, and to calculate the sterilant vapor concentration from the absorbance value. The microprocessor is also preferably adapted to generate an output signal proportional to the sterilant vapor concentration. The system further includes a controller to receive the output signal and to variably control addition of the sterilant vapor to the sterilization chamber to maintain a selected concentration and/or percent saturation of the sterilant vapor in the sterilization chamber in response to the received output signal. In the course of determining the concentration of hydrogen peroxide vapor, the microprocessor is preferably programmed to determine the absorbance due substantially only to hydrogen peroxide, and to compare this absorbance to a reference absorbance determined by a calibration procedure described more fully hereinbelow.

In a preferred embodiment of the invention, the system utilizes an infrared ("IR") sensor probe integrated into the monitoring subsystem which is thereby enabled to monitor the concentration of the hydrogen peroxide vapor at one or more selected locations in or portions of the sterilization chamber. The sensor probe provides for passage of a beam of electromagnetic radiation, preferably having wavelengths in the infrared region, through the sterilant vapor in the sterilization chamber. Some of the radiation is absorbed by the vapor, and the unabsorbed radiation returns to a radiation detector sensitive to wavelengths of radiation in the IR region of the electromagnetic spectrum, which determines the amount of radiation absorbed by the vapor, and provides an absorbance signal to a microprocessor which calculates the concentration of hydrogen peroxide vapor in the sterilization chamber. The concentration thus obtained is converted into an analog signal which the process control subsystem uses to control operation of the sterilization apparatus. The sterilization apparatus comprises the chamber, valves, pumps, heaters, and other sterilization-related equipment. Operation of the various elements of this apparatus variously affect and control the concentration of hydrogen peroxide vapor in the sterilization chamber, in order to obtain an optimum level of sterilization efficiently and economically. The present invention provides a new and significant increase in the levels of both control and economy to the hydrogen peroxide vapor sterilization process.

BRIEF DESCRIPTION OF THE DRAWINGS

The present invention can be better understood by reference to the drawings in which.

DETAILED DESCRIPTION OF THE INVENTION

The sterilant vapor comprises hydrogen peroxide vapor generated from an aqueous hydrogen peroxide solution having a concentration in the range from 3–98% by weight; preferably the concentration of aqueous hydrogen peroxide is from 5–95% by weight; and most preferably it is in the range from 30–35% by weight. The carrier gas in the flow-through system preferably comprises air. The internal pressure in the deep vacuum sterilization chamber is preferably in the range of about 0.1 to 10 torr. When hydrogen peroxide vapor is the sterilant vapor used with this invention, the concentration of hydrogen peroxide vapor is most preferably in the range of 1 to 5 milligrams per liter, preferably up to about 10 milligrams per liter, but may be higher, as long as condensation or saturation is avoided.

It is contemplated that other gaseous sterilants may be employed in the system and be subjected to the method described herein. In the flow-through systems, other inert gas carriers, such as air, nitrogen, or helium may also be used. For purposes of describing the preferred embodiments of the flow-through system, the carrier gas and the sterilant vapor discussed will be respectively air and vapor phase hydrogen peroxide generated from aqueous hydrogen peroxide solution. For purposes of describing the preferred embodiments of the deep vacuum system, the sterilant vapor will be vapor phase hydrogen peroxide generated from aqueous hydrogen peroxide solution. Thus, water vapor will be present in variable concentrations in the sterilization chamber of both the flow-through and the deep vacuum embodiments.

The concentration of hydrogen peroxide vapor, or other sterilant vapor, is preferably determined on a weight per volume basis. The weight is preferably expressed in milligrams, while the volume is preferably expressed in liters. The volume is the volume within which the sterilant vapor is dispersed. In a deep vacuum system, the volume measured is generally that of the sterilization chamber only. In a flow-through system, the volume is the total volume of circulating carrier or multicomponent gas.

In the system, an IR sensor probe is mounted within the sterilization chamber, or some portion of the sterilization system in fluid contact with the sterilization chamber, for measuring the absorbance of sterilant vapors in the chamber or system. In the preferred embodiment, in order to determine the concentration of hydrogen peroxide vapor, the absorbance of IR radiation at two or more wavelengths is measured. One wavelength in the IR region is selected at which water alone absorbs energy, and another wavelength in the IR region is selected at which hydrogen peroxide absorbs energy. Generally, the wavelengths most strongly absorbed by hydrogen peroxide are also absorbed by water. Therefore, to obtain the absorbance due only to hydrogen peroxide, it is necessary to adjust the absorbance signal obtained for the combined water and hydrogen peroxide for the energy absorbed by water at that wavelength. The adjusted absorbance signal thus obtained represents the absorbance due to hydrogen peroxide only, and can be used to directly calculate the concentration of hydrogen peroxide.

In the system, the absorbances determined at the first and second wavelengths are transmitted to a microprocessor programmed to calculate the concentration of hydrogen peroxide vapor in the sterilization chamber. The output of this microprocessor may be a digital signal. Preferably, the microprocessor has been pre-programmed with calibration values derived from controlled experiments to calibrate the instruments with known concentrations of hydrogen peroxide vapor in the multicomponent vapor. An example of calibration of the system is included hereinbelow.

The digital signal obtained initially from the microprocessor is converted into an analog signal. The analog signal is transmitted to apparatus to control operation of the liquid hydrogen peroxide injection valve into the vaporizer, so as to maintain an optimum concentration of hydrogen peroxide vapor in the sterilization chamber.

Figure 1:
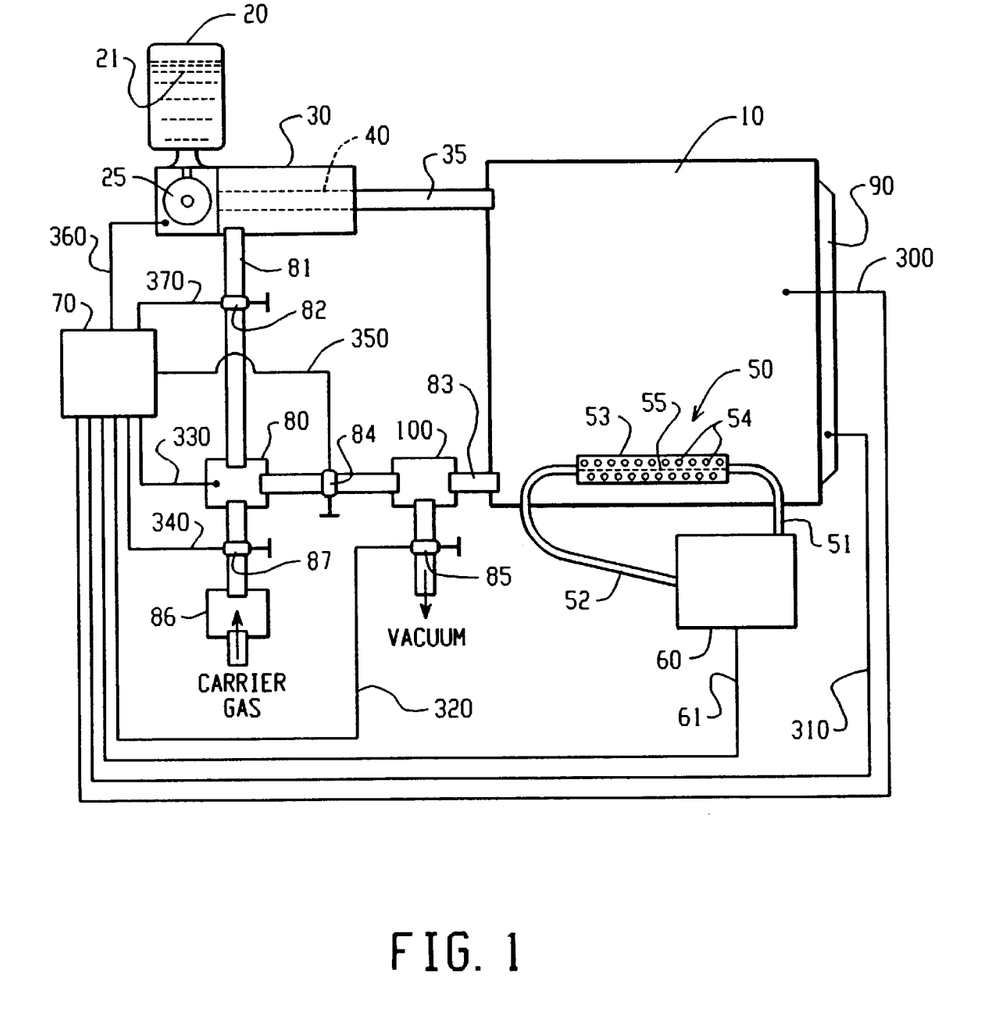
FIG. 1 is a schematic illustration of a real-time monitoring and control system for optimizing parameters including the concentration of one or more sterilant vapors in a multicomponent vapor sterilization process.

With reference to FIG. 1, a generalized schematic illustration of the invention is shown. A sterilization chamber 10 is provided in which sterilization of objects is carried out. Alternatively, chamber 10 might be some other type of chamber, such as a glove-box, which needs to be sterilized. In any case, the sterilization chamber 10 is supplied with a vapor formed from a liquid sterilant 21 contained in a liquid sterilant reservoir 20. The liquid 21 in the reservoir 20, may be an aqueous solution of hydrogen peroxide between 3 and 98% by weight, is preferably an aqueous solution of 10–50% hydrogen peroxide by weight, and, as previously mentioned, is most preferably an aqueous solution of 30–35% hydrogen peroxide by weight. Aliquots of the liquid 21 are metered from the reservoir 20 through a valve 25 as controlled by a microprocessor-controller 70, communicated via a connector 360. Each aliquot of liquid 21 is deposited into a vaporizer 30 which is in turn equipped with a heated surface 40. Operation of such a vaporization apparatus is more fully described in U.S. Pat. No. Re. 33,007, as described previously and incorporated herein by reference. The entire aliquot of sterilant liquid 21 (sterilant and water) is flash vaporized in the vaporizer 30 to form the sterilant vapor, such that the relative composition of the vaporized sterilant is substantially the same as that of the liquid sterilant from which it was vaporized. The vaporized sterilant passes through an inlet port 35 into the sterilization chamber 10.

In further reference to FIG. 1, in the case of a flow-through sterilization system, a carrier gas continuously flows from a carrier gas source through inlet tube 81 into vaporizer 30, in which the carrier gas and the vaporized sterilant combine, following which the combined carrier gas and sterilant vapor pass through inlet port 35, and into the sterilization chamber 10. The carrier gas source (not shown) may be a compressor (e.g., for air), or a cylinder or tank of compressed gas, or air at atmospheric pressure for systems operating at negative gauge pressure. Flow of the carrier gas into the system is regulated by a carrier gas inlet valve 87, while flow of recirculating carrier gas and sterilant vapor is controlled by a recirculating flow control valve 82. The valves 82 and 87 are preferably operated under the control of a process control portion of the microprocessor-controller 70, communicated via connectors 370 and 340. The valves 82 and 87, like other equipment in the apparatus, may also operate under the control of a separate process controller, which in turn operates in response to an analog signal output from, e.g., a microprocessor in an IR unit 60.

Referring still to FIG. 1, the incoming carrier gas preferably passes through a sterile filter 86 and may optionally be dried while passing through a carrier gas dryer 80, the latter of which is operated primarily to control the water content of the recirculating carrier gas. The dryer 80 may be operated under the control of the microprocessor-controller 70, communicated via a connector 330, depending on how the microprocessor-controller is programmed.

In an embodiment of FIG. 1 having an open flow-through system, the dryer 80 may be either absent or replaced by a heater to raise the temperature of the incoming carrier gas to a selected sterilization temperature.

As shown in FIG. 1, the carrier gas exits the sterilization chamber 10 by means of an outlet port 83, through a catalytic decomposition device 100, a carrier gas outlet valve 84, through the heater/dryer 80 for heating or drying, and then is recirculated through the closed-loop flow-through system.

The flow-through system may also be operated as an open system, by closing valve 84 and opening the valve 85, thereby removing carrier gas from the chamber 10 to atmosphere. In such an embodiment, in which a deep vacuum may not be necessary, the vacuum pump may be replaced by another type of pump for removal of carrier gas. Preferably, operation of the valves 84 and 85 are controlled via connectors 350 and 320, respectively, as shown in FIG. 1. Preferably, the catalytic decomposition device 100 is operated to decompose any remaining sterilant vapor into harmless by-products, leaving the recirculating carrier gas free of sterilant and requiring a new supply of sterilant vapor to reach its selected concentration. Alternatively, the carrier gas may be recirculated with its load of remaining sterilant vapor, and in this case a quantity of sterilant vapor will be added sufficient only to replenish the sterilant vapor to its selected concentration.

If the apparatus shown in FIG. 1 is to be operated as a deep-vacuum sterilization system, the carrier gas apparatus just described will either not be used or not be part of the apparatus at all, valves 82 and 84 remaining closed at all times, except to open the system to an external atmosphere and release the deep vacuum.

The outlet port 83, in a deep-vacuum embodiment of FIG. 1, like the flow-through embodiment, is attached first to the catalytic decomposition device 100, thence to a vacuum pump (not shown) via an outlet valve 85. The vacuum pump creates the deep vacuum required for such an embodiment. As in other embodiments, the catalytic decomposition device 100 decomposes hydrogen peroxide into water and oxygen. The description of FIG. 5 below provides further detail applicable to a deep vacuum sterilization method in accordance with the present invention.

If the sensor probe 50 of the present invention is employed with the closed flow-through system, use of the catalytic decomposition device 100 is optional. As the sensor 50 can detect the concentration of hydrogen peroxide or other sterilant gases on a real-time basis, only sufficient vapor need be added to the chamber to maintain the selected concentration of hydrogen peroxide or other sterilant vapor in the sterilization chamber 10.

In the deep vacuum and open flow-through embodiments, since the hydrogen peroxide vapor or other sterilant vapor is to be exhausted on completion of the sterilization cycle, the catalytic decomposition device 100 is preferably operated to decompose the vapor.

Continuing to refer to FIG. 1, the sterilization chamber 10 is equipped with a heater 90, for providing heat as needed for sterilizations carried out at temperatures above room temperature. It will be understood that the heater 90 may be operated under the control of the microprocessor-controller 70, via a connector 310, depending on how the microprocessor-controller is programmed. Alternatively, the carrier gas may be heated prior to its introduction into either the system as a whole or the sterilization chamber 10.

The microprocessor-controller 70, as shown in FIG. 1, is preferably connected via connector 300 with a plurality of sensors disposed with the sterilization chamber 10. These sensors provide information on, e.g., temperature, pressure, humidity, and other relevant conditions within the chamber 10. This information is used by the microprocessor portion of microprocessor-controller 70 according to its programming to provide control of operation of the sterilizer system via the controller portion of the microprocessor-controller 70.

Figure 3:
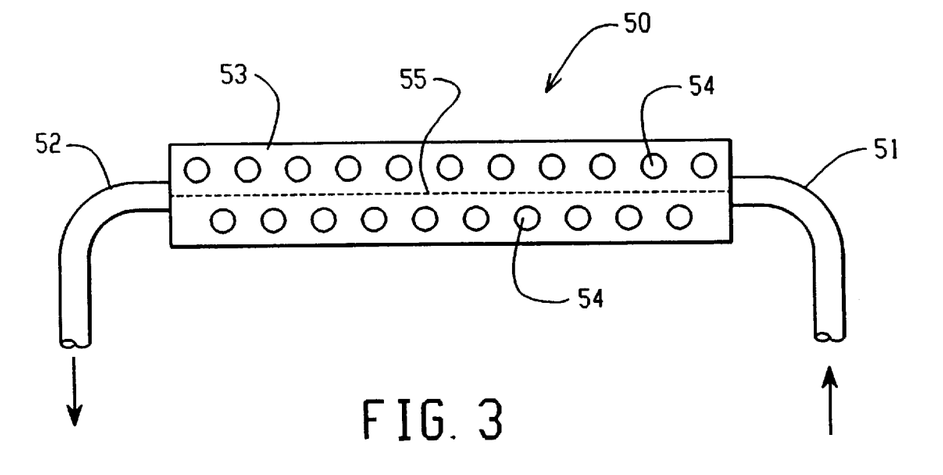
FIG. 3 is a schematic illustration of one embodiment of an infrared sensor probe for use with the system of FIG. 1.

The sterilization chamber 10 is further provided with a sensor probe 50. The sensor probe 50 of the preferred embodiment is an infrared sensor probe. Two possible embodiments of the sensor probe 50 are depicted schematically in FIGS. 3 and 4.

The sensor probe 50 is preferably configured in a self-contained unit as shown in FIG. 1, position B of FIG. 2, and FIGS. 3–6, in which a transmitting and receiving means are attached to a body 53. The transmitting means 51 transmits radiation from a radiation source to the sensor probe 50. The receiving means 52 receives radiation exiting the sensor probe 50 for return to a radiation detector. The body 53 acts both as a positioner for maintaining the alignment of the transmitting and receiving means, and as a shield to prevent objects within the sterilization chamber 10 from obstructing an energy path 55 (shown in phantom) between the transmitting and receiving means. The path 55 is defined by the radiation traveling from transmitting means 51 to receiving means 52. Preferably the body 53 encloses the path 55, in order to prevent blockage of the path by articles or materials in the sterilization chamber 10. Preferably the body 53 comprises a plurality of openings 54, through which the sterilant vapor to be measured may freely pass. The openings 54 allow free passage and exchange of the sterilant vapor into and out of the path of the radiation beam, whereby the sterilant vapor interacting with the radiation is representative of that in the sterilization chamber 10. Preferably the openings 54 in the body 53 have the maximum size possible so as to allow the sterilant vapor to pass most freely, consistent with preventing objects in the sterilization chamber 10 from obstructing the energy path 55.

Figure 2:
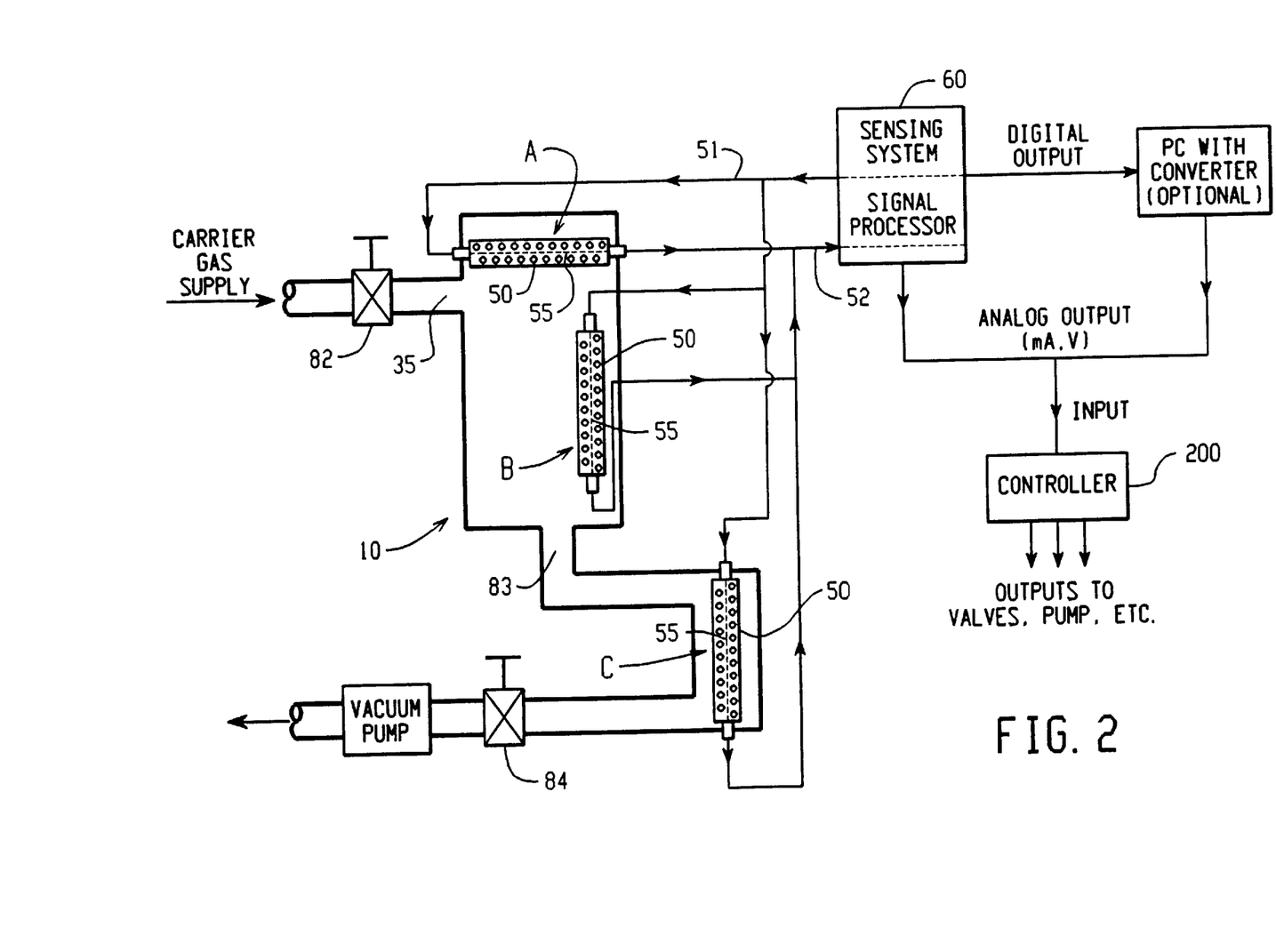
FIG. 2 is a schematic illustration of another embodiment of the monitoring and control system, demonstrating three possible locations for the infrared sensor probe in various portions of the sterilization chamber of the system.

With reference to FIG. 2, which is a schematic illustration of another embodiment of the monitoring and control system, three possible locations for the infrared sensor probe 50 in the sterilization chamber 10 are shown. The three positions in FIG. 2 are designated A, B, and C. Position A has the sensor probe 50 mounted adjacent the inlet port 35. Since position A is closest to the inlet port 35, it may result in the highest readings for hydrogen peroxide concentration. Position B has the sensor probe in a position somewhat removed from both the inlet port 35 and the outlet port 83. Position B may be closest to the load to be sterilized, and the hydrogen peroxide concentration there may be more representative of the concentration experienced by the load. Position C has the sensor probe in the outlet port 83. This position may yield the lowest readings for hydrogen peroxide concentration, but if it is desired to maintain some threshold minimum hydrogen peroxide concentration, this location should give the best results. The actual placement of the sensor probe 50 may best be determined by the user, in view of the exact application for which the sterilization system is employed. More than one sensor probe 50 can be mounted within the system, and the microprocessor may be programmed to select only one or more than one sensor probe 50 when a plurality of the sensor probes 50 are employed.

Figure 4:
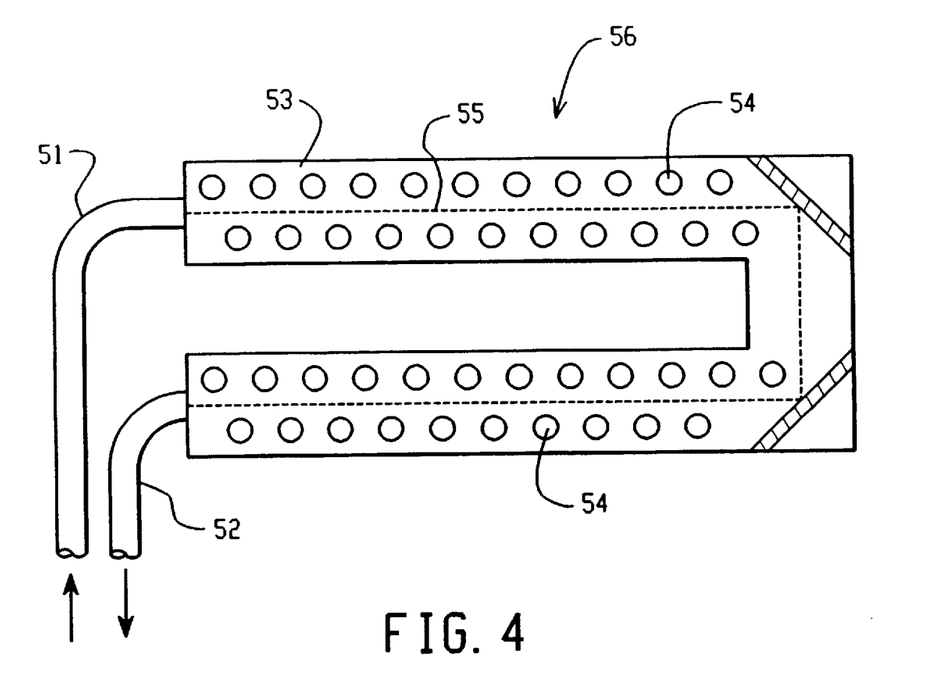
FIG. 4 is a schematic illustration of another embodiment of an infrared sensor probe for use with the system of FIG. 1.

Preferably the sensor probe 50 is as compact as possible. To achieve the desired compactness, a sensor probe 56, as shown in FIG. 4, or a similar device may be employed. The sensor probe 56 shown in FIG. 4 allows a path length approximately about two times longer than that of the embodiment of FIG. 3, while the actual length of the sensor probe 56 is reduced by about half over that of the sensor probe 50. Such increase in path length and concomitant reduction in overall size may be achieved by using mirrors, prisms, magnets, or other energy reflecting or bending devices to bend or reverse the direction of the electromagnetic radiation passing through the sensor probe 50. The mirrors, prisms, magnets, or other energy reflecting or bending devices may be employed to make multiple reflections or bends, thus further reducing the size of the probe relative to the path length of the electromagnetic radiation. The path length selected is that sufficient to provide a useful signal for measurement by the detector in the IR unit 60, and determines the number of reflections needed to provide that path length within the confines of the particular system of interest to the user.

Other embodiments of the sensor probe 50, such as those shown at positions A and C in FIG. 2, include structures which have no actual body (such as the body 53). In such embodiments, the transmitting and receiving means are directly attached to the walls of the sterilization chamber 10, such as is shown in position A of FIG. 2, or to the walls in other portions of the system adjacent the sterilization chamber 10, such as is shown in position C of FIG. 2. Such mounting should be sufficiently secure to provide that the IR beam passing from the transmitting means to the receiving means remain in alignment. As with other embodiments, in this embodiment a path 55 is defined by the IR beam between the transmitting and receiving means.

Furthermore, in these embodiments steps are preferably taken to insure that the energy path 55 taken by the IR beam does not become obstructed by articles in the load to be sterilized. A shield could be used for this purpose when the probe is mounted in the sterilization chamber. A shield may not be needed if the sensor probe is mounted as shown in position C of FIG. 2, since articles would not normally be in that portion of the chamber. As was described for the preferred embodiment of sensor probe 50, the shield would have large openings, the size of the openings limited only by the requirement that the shielding function not be lost.

Whether the sensor probe 50 or some other embodiment is employed, techniques known to those of ordinary skill in the art for increasing path length may be employed as needed. These techniques particularly include a plurality of reflections of the IR beam within the sterilization chamber 10.

All portions of the sensor probe 50 and of the entire system that will come into contact with hydrogen peroxide are preferably made of a material which is both inert to hydrogen peroxide and which do not absorb or adsorb hydrogen peroxide. Accordingly, the body 53 is preferably made of passivated or electro-polished stainless steel or passivated aluminum. Other materials which do not interact deleteriously with hydrogen peroxide include glass, polytetrafluoroethylene (PTFE, Teflon®), and viton. The body 53 preferably has openings at either end for secure attachment of the transmitting and receiving means. Preferably the body 53 includes means for maintaining the transmitting and receiving means in proper alignment, so as to maximize signal strength therebetween. Sensor probe 50 may also comprise lenses at the probe-attaching ends of the transmitting and receiving means, for focusing and realigning the beams of radiation carried by the transmitting and receiving means.

The preferred transmitting and receiving means are both fiber optic cables, designated 51 and 52, respectively, in FIGS. 1–6. The fiber optic cables 51 and 52 are preferably approximately 5–20 meters in length, but may be up to at least 200 meters in length. Maximum length depends to some degree on the wavelength of radiation carried by the cables. In the case of the preferred infrared radiation, a maximum of 200 meters is applicable. The fiber optic cable 51 transmits the preferred infrared radiation from an infrared source in the IR unit 60, to the sensor probe 50, and fiber optic cable 52 returns the unabsorbed portion of the infrared radiation back to the IR unit 60. All portions of the fiber optic cables 51 and 52 exposed to hydrogen peroxide vapor within the sterilization chamber 10 are preferably coated with Teflon® so as to be fully inert to the hydrogen peroxide.

The IR unit 60 preferably comprises an infrared source, an infrared radiation detector, and a microprocessor programmed to calculate the concentration of hydrogen peroxide in the sterilization chamber 10 based on the information transmitted by the fiber optic cables 51 and 52. A suitable IR unit with a sensor probe is available from Guided Wave Inc., El Dorado Hills, Calif.

The microprocessor of IR unit 60 is operably connected to the microprocessor-controller 70. It will be understood that the microprocessor of IR unit 60 may be combined with the microprocessor portion of microprocessor-controller 70 into a single microprocessor, and that the output of this single microprocessor would in turn provide signals to a controller. If the microprocessors are combined, the output preferably provides an analog signal directly to a controller to control operation of the sterilization chamber 10 in a manner similar to that described for the output of the microprocessor-controller 70.

Referring again to FIG. 1, the microprocessor contained in the IR unit 60 is preferably programmed to receive data from the sensor probe 50, and to calculate therefrom the concentration of sterilant vapor in sterilization chamber 10. In this embodiment, the microprocessor-controller 70 is programmed to receive only the sterilant vapor concentration values determined by the microprocessor of the IR unit 60, and to make its own determination of sterilant vapor needed to be added to sterilization chamber 10, based on input from the microprocessor of the IR unit 60, the temperature, pressure, and other parameters of the sterilizing chamber 10 made available to it. The microprocessor of the IR unit 60 may also be programmed to calculate the quantities of sterilant vapor needed to be added to the sterilizing chamber 10 and to signal the microprocessor-controller 70 via connector 360 to cause the sterilant liquid 21 to be injected into the vaporizer 30, accordingly, to produce the sterilant vapor.

The IR unit 60 includes an IR source, an IR detector, and an analyzer, preferably a microprocessor, for calculating the concentration of the sterilant vapor. The IR source and IR detector are respectively capable of producing and quantitatively detecting IR radiation at least at the selected wavelengths. The IR unit 60 preferably operates as follows. Output from a source of IR radiation is directed down the transmitting means, preferably the fiber optic cable 51, and through the vapors contained in the sterilization chamber 10. Radiation not absorbed by the multicomponent vapor returns through the receiving means, preferably the fiber optic cable 52, to an IR detector in the IR unit 60.

The IR source is capable of providing radiation at substantially the selected wavelengths or across a range or spectrum of wavelengths. As described, the selected wavelengths may be two or more. At least one selected wavelength should be unique to at least one component of the multicomponent vapor. In the preferred embodiment of the present invention a first wavelength, at which water, but not hydrogen peroxide, absorbs IR radiation is selected, and a second wavelength, at which both water and hydrogen peroxide absorb IR radiation, is selected.

The IR detector is able to detect the strength of both the returning signal and of the transmitted signal, and to provide this information to the microprocessor in the IR unit 60. The IR detector produces a signal proportional to the absorbance at each wavelength in the IR spectrum, or at least of the absorbance at the selected wavelengths.

The microprocessor contained in the IR unit 60 is programmed to calculate the concentration of hydrogen peroxide vapor in the multicomponent vapor by comparing absorbances at the selected wavelengths. The procedure involves correction of the combined absorbance of the IR wavelength at which both hydrogen peroxide and water absorb, for the portion of the combined absorbance due to water, in order to obtain an absorbance value solely due to the hydrogen peroxide in the sterilant vapor. The absorbance due to water is determined by reference to the absorbance peak due solely to water. The microprocessor in the IR unit 60 is programmed to make this determination by comparing the absorbances at the wavelengths of interest with absorbances for standardized concentrations of hydrogen peroxide vapor and water vapor.

In a preferred embodiment, a microprocessor in the IR unit 60 provides a digital readout of the concentration of hydrogen peroxide vapor and a digital or analog output signal to the microprocessor-controller 70, shown in FIG. 1, or other process control device. In another embodiment, shown in FIG. 2, the IR unit 60 may provide an analog signal output which allows controller 200 to directly control operation of the sterilizer system. As an alternative, also shown in FIG. 2, the IR unit 60 may provide a digital output, which is fed into a converter which may be included in a personal computer (PC), which converts the signal to an analog output for transmission to the controller 200. In another embodiment, shown in FIG. 5, and similar to that shown in FIG. 1 but for a flow-through system, the microprocessor in the IR unit 60 provides a digital output signal via a connector 61 to the microprocessor portion of the microprocessor-controller 70. In microprocessor-controller 70 the signal is integrated with other operational signals, such as temperature, pressure, and relative humidity, obtained directly from devices in the chamber 10 by way of a connector 300. The output from the microprocessor-controller 70 is preferably a plurality of analog signals, output from the controller portion of the microprocessor-controller 70 to directly control operation of the various components of the sterilizer system. For example, as shown in FIG. 1, signals from the microprocessor-controller 70 may control the temperature in the chamber via a connector 310 to the heater 90, may control the pressure in the chamber via operation of a connector 320 to the valve 85. As shown in FIG. 1, signals from the microprocessor-controller 70 may control operation of the dryer 80 via the connector 330, and may control flow of carrier gas into the system via the connector 340 to the valve 87. Finally, as shown in FIG. 1, microprocessor-controller 70 may control whether the system is operated as a flow-through or deep vacuum system through its connection to valve 84 via connector 350 and valve 82 via connector 370.

The optimum hydrogen peroxide vapor concentration and/or percent saturation are functions of several different variable conditions in the sterilization process. In a preferred embodiment, the microprocessor portion of the microprocessor-controller 70 is programmed to calculate the optimum hydrogen peroxide concentration and/or percent saturation based on the variable conditions under which the sterilization apparatus is being operated.

A preferred method of calculating the percent saturation in a flow-through system is described in U.S. application Ser. No. 08/237,406, entitled "Optimum Hydrogen Peroxide Vapor Sterilization Method," filed on May 2, 1994, and now U.S. Pat. No. 5,445,792 issued Aug. 29, 1995, which has been incorporated herein by reference.

The most preferred system for monitoring and controlling the sterilant vapor concentration is also capable of monitoring and controlling other relevant parameters, including temperature, pressure, humidity and relative humidity. Accordingly, the system preferably includes either a means of directly measuring the water content (humidity) in the sterilization chamber, particularly in deep vacuum and closed flow-through systems, or of estimating the water content based on the relative humidity of air entering the system in an open flow-through system. The values obtained for water content are most preferably entered into the microprocessor-controller in order to allow control of relevant system parameters, according to the programming of the microprocessor. The water content of the circulating carrier gas may be controlled in flow-through systems so equipped by use of a dryer. In deep vacuum systems, the water content, as discussed above, is a function of the pressure, so by maintaining a very low pressure, the water content may be kept within acceptable limits.

The IR sensor probe 50 or other sensor probe used with the system of the present invention needs to be calibrated to known concentrations of hydrogen peroxide vapor. Such calibration using the IR sensor probe 50 is described below for a flow-through hydrogen peroxide vapor sterilization apparatus. Calibration of a deep vacuum hydrogen peroxide vapor apparatus would proceed in generally the same manner as the flow-through system.

Referring to the general schematic illustration of FIG. 1, the sensor probe 50 mounted within the sterilization chamber 10 is bathed in a flow of carrier gas and a first concentration of hydrogen peroxide vapor passing through the sterilization chamber 10. Preferably, the temperature and pressure of the calibration procedure is close to that of the actual sterilization process. Preferably, in order to maintain a reasonably constant level of hydrogen peroxide vapor in the chamber 10, the chamber 10 has no load during the calibration operation.

The IR unit 60 is operated to determine the absorbance at the selected wavelengths for the first hydrogen peroxide vapor concentration. Through an opening (not shown) in or within the sterilization chamber, one or more aliquots of the circulating multicomponent vapor are collected and trapped by suitable means for each hydrogen peroxide vapor concentration to be determined for the standard curve.

Preferably, the collection proceeds by bubbling the multicomponent vapor through water or a colorimetric reagent which will rapidly react with the hydrogen peroxide component of the vapor and produce a measurable irreversible color change in the reagent. The amount of hydrogen peroxide in the solution can be determined using a calorimetric reagent such as xylenol orange dye. In the presence of ferrous ion and acid, the hydrogen peroxide oxidizes the ferrous ion to a ferric ion, which then complexes with the xylenol orange to produce a measurable color change. The color change is measured by known means, and the concentration of hydrogen peroxide determined therefrom. This concentration of hydrogen peroxide vapor and the corresponding IR absorbance readings for both the first and second wavelengths from the IR analyzer are recorded. These absorbances have a strength proportional to the concentration of hydrogen peroxide vapor and the other vapor or multicomponent vapor, respectively. As previously stated, preferably the other vapor is water vapor, and the multicomponent vapor consists essentially of hydrogen peroxide vapor and water vapor.

As with the actual determinations during a sterilization process, the microprocessor of the IR unit 60 is preferably programmed to determine the absorbance value due solely to the hydrogen peroxide vapor.

The steps of the calibration process are repeated at least two more times at second and third concentrations of hydrogen peroxide vapor in the multicomponent vapor flowing through the sterilization chamber 10. Preferably, the temperature and pressure of the second and third and any subsequent calibration procedures are close to the same as those for the first calibration, and all are comparable to those of the actual sterilization process.

The IR absorbances for each concentration of hydrogen peroxide vapor at the selected wavelengths are then compared with the concentrations of hydrogen peroxide vapor determined by the calorimetric analysis. A standard curve is thus obtained relating absorbance due to hydrogen peroxide with the chemically determined hydrogen peroxide concentration. The standard curve is used to generate a reference absorbance value per unit concentration of hydrogen peroxide and per unit path length, also known as an extinction coefficient.

The extinction coefficient and the path length of the probe are entered into the microprocessor of the IR unit 60, for use in calculating the sterilant concentration in the multicomponent vapor.

When an unknown concentration of hydrogen peroxide is to be determined by the sensor probe 50 in the preferred embodiment of the present invention, absorbances at the two selected wavelengths are obtained, as described above. The microprocessor is preferably programmed to compare the absorbance for both hydrogen peroxide and water with the absorbance due only to water in the sterilization chamber 10, in order to determine the absorbance due only to hydrogen peroxide. This absorbance due to hydrogen peroxide is then used along with the extinction coefficient and path length values stored in the microprocessor to calculate the actual concentration of hydrogen peroxide vapor in the sterilization chamber 10.

Inspection of FIG. 1 reveals that the apparatus schematically shown therein may be operated in a combination of the deep vacuum and flow-through procedures. Such a combination would generally involve initial deep vacuum steps, in which a deep vacuum removes air and moisture from the sterilization chamber 10, followed by a step of closed system injection of vapor. These initial steps are followed by non-deep vacuum steps providing a carrier gas flow to the sterilization chamber 10 and further introduction of sterilant vapor. The deep vacuum steps and non-deep vacuum steps are repeated in alternating fashion. A similar process is more fully described in copending, commonly assigned U.S. patent application Ser. No. 08/279,688, filed Jul. 25, 1994, which has been incorporated herein by reference.

Figure 5:
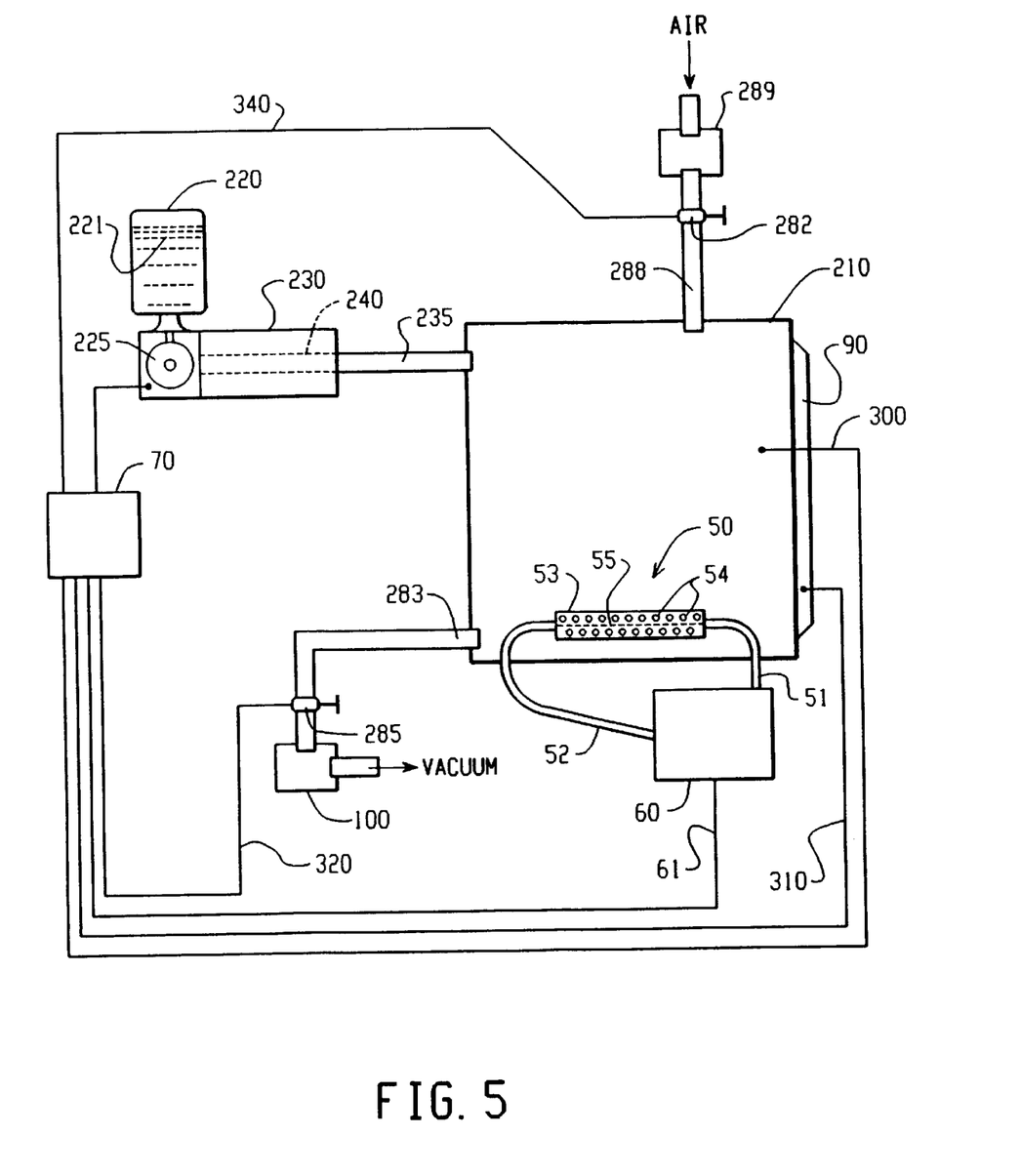
FIG. 5 is a schematic illustration of a preferred embodiment of the monitoring and control system in use with a deep vacuum sterilization process, similar to FIG. 1.

With reference to FIG. 5, which is a schematic illustration of a preferred embodiment of the monitoring and control system in use with a deep vacuum sterilization process, the system is briefly described in the following. More detailed descriptions of the operation of a deep vacuum hydrogen peroxide vapor sterilization may be found in U.S. Pat. No. Re. 33,007, Aug. 1, 1989, and U.S. Pat. No. 4,956,145, Sept. 11, 1990, both incorporated herein by reference.

Review of FIG. 5 reveals its similarity to FIG. 1, without the flow-through portion of the apparatus. FIG. 5 shows an apparatus including a sterilization chamber 210, a vaporizer 230, and a liquid reservoir 220, containing a liquid sterilant 221. A valve 225 meters the liquid 221 onto the heated surface 240 of the vaporizer 230. The vaporizer 230 is in open, fluid communication, through inlet port 235, with the vacuum chamber 210. A vacuum pump maintains the deep vacuum, pulling the vacuum through the outlet valve 285, as controlled via connector 320, and an outlet port 283. As in the system of FIG. 1, the system of FIG. 5 may include a catalytic decomposition device 100 for destroying hydrogen peroxide exiting the sterilization chamber 210.

The sterilization chamber 210 is equipped with a heater 90, for providing heat as needed for sterilizations carried out at temperatures above room temperature. It will be understood that the heater 90 may be operated under the control of the microprocessor-controller 70, via connector 310, depending on how the microprocessor-controller is programmed, as has been described with reference to FIG. 1.

The sterilization chamber 210 is further provided with a sensor probe 50, as previously described. Operation of the sensor probe 50 is essentially the same whether in deep vacuum mode or in flow-through mode. Similarly, operation of the IR unit 60 and microprocessor-controller 70 are substantially the same in the deep vacuum mode as described with reference to FIG. 1.

The system shown in FIG. 5 includes a source of sterile air for venting the chamber when the deep vacuum is to be broken. Thus, air is allowed to pass through a sterile filter 289 through an inlet port 288, its flow controlled by operation of a valve 282. Operation of the valve 282 may be under the control of the microprocessor-controller 70, via a connector 340.

Figure 6:
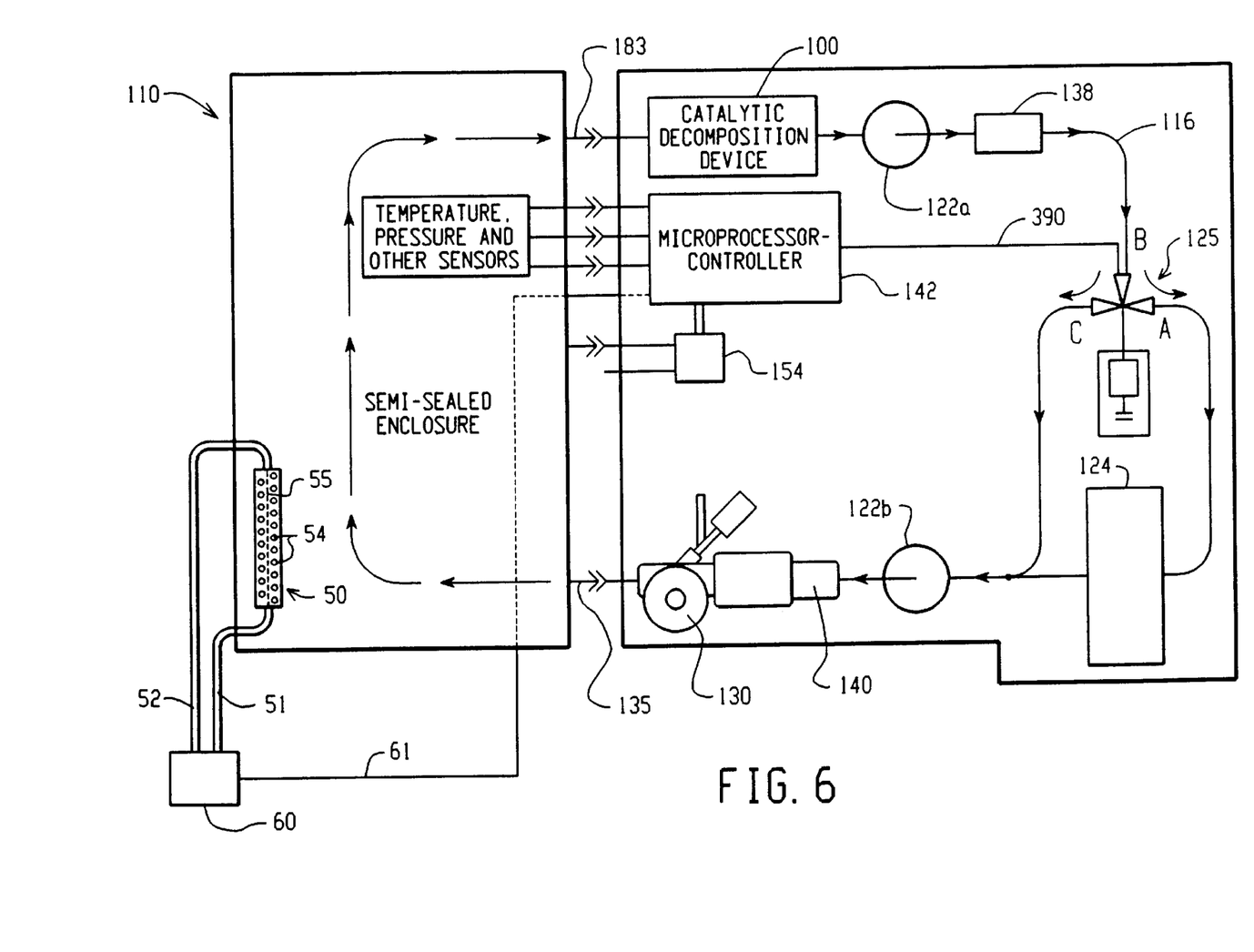
FIG. 6 is a schematic illustration of a preferred embodiment of the monitoring and control system in use with a flow-through sterilization process.

In one preferred embodiment of the invention, known as a "closed flow-through" system, a flow of carrier gas is recirculated in a closed-loop conduit circuit that leads into, through, and out of a sealable chamber. A schematic illustration of such a system is shown in FIG. 6. A liquid sterilant is vaporized and delivered into the carrier gas flow entering the chamber, and then converted to a form suitable for disposal after exiting the chamber.

The carrier gas preferably comprises air. The liquid sterilant preferably comprises aqueous hydrogen peroxide, and the vaporized hydrogen peroxide sterilant exiting the sterilization chamber 110 is preferably converted to water and oxygen with a catalytic decomposition device.

The flow-through vapor phase decontamination system of the invention includes a sealable chamber having an inlet port and an outlet port. A conduit circuit is fluidly connected to the sterilization chamber inlet and outlet ports to provide a closed-loop flow path for recirculating a carrier gas into, through, and out of the chamber. The system may also include a blowing unit and an adjustable drying or heating unit, each fluidly connected to the conduit circuit. The blowers 122a and 122b serve to push or force the carrier gas around the closed-loop flow path. The adjustable drying unit 124 serves to selectively dry the carrier gas flow entering the chamber, and may also include a heater to heat the carrier gas.

The system of FIG. 6 also includes a liquid vaporizer unit 130 for delivering a vaporized liquid sterilant into the carrier gas flow. The vaporizer unit is fluidly connected to the conduit circuit between the drying unit and the chamber inlet port. In addition, the system includes a catalytic decomposition device 100 for converting the sterilant vapor to a form suitable for disposal, fluidly connected to the conduit circuit downstream of the chamber outlet port 183. When the sterilant vapor is hydrogen peroxide, the catalytic decomposition device decomposes the hydrogen peroxide to water and oxygen.

The system preferably also includes provision for monitoring the temperature, pressure, humidity and relative humidity within the chamber during decontamination.

The method of the invention will now be described with particular reference to the exemplary system illustrated in FIG. 6. As shown, the flow-through vapor phase sterilization system of the invention includes a sealable sterilization chamber 110 having an inlet port 135 and an outlet port 183. A conduit circuit 116 is fluidly connected to the chamber inlet and outlet ports to provide a closed-loop flow path for recirculating a carrier gas into, through, and out of the chamber 110.

AS shown in FIG. 6, the liquid sterilant vaporizer 130 vaporizes an aliquot of aqueous hydrogen peroxide and delivers the vapor into the carrier gas flow. The hydrogen peroxide vapor passes through inlet port 135, into and through the sterilization chamber 110, and exits via exit port 183. The carrier gas and hydrogen peroxide vapor, together with water vapor comprising the multicomponent vapor, may then flow into the catalytic decomposition device 100 for conversion into water and oxygen. The flow of multicomponent gas (with or without the hydrogen peroxide vapor, depending on whether the decomposition device 100 is being operated) proceeds under the influence of the blower 122a. A variable position valve 125 controls whether the flow of carrier gas proceeds to or bypasses the dryer 124, under the control of the microprocessor 142, communicated via connector 390. The flow of multicomponent gas is further driven by the second blower 122b. Preferably, the blowers can be adjusted based on feedback from flow sensors 138 and 140 to provide a slightly negative or positive pressure within the sterilization chamber 110 as monitored by a pressure transducer 154.

The multicomponent gas next flows through the vaporizer 130, into which an aliquot of aqueous hydrogen peroxide is injected. The size of the aliquot injected is preferably determined by the microprocessor-controller 142 to maintain the selected concentration of hydrogen peroxide vapor in the sterilization chamber 110. The multicomponent gas with its newly added hydrogen peroxide vapor then passes through inlet port 135 into the sterilization chamber 110, into contact with the load of articles and materials to be sterilized, and into contact with the radiation passing along the path 55 in sensor probe 50. The multicomponent vapor passing through the sensor probe 50 absorbs some quantum of the preferred IR wavelengths. The absorptions are due both to hydrogen peroxide and to water.

If a solvent other than water is used in the liquid sterilant solution, its IR absorption at its characteristic wavelength is determined at this time, as is the IR absorption of a sterilant vapor other than hydrogen peroxide, if such a vapor is used as the sterilant.

As previously described, the absorption data are then used to determine the concentration of hydrogen peroxide vapor in the sterilization chamber 110, and therefrom to control addition of further hydrogen peroxide.

As shown in FIG. 6, an IR sensor probe 50 is mounted within the semi-sealable sterilization enclosure 110. Transmitting and receiving means are preferably fiber optic cables 51 and 52, respectively. The fiber optic cables 51 and 52 are attached to the IR unit 60, which includes output connection 61 to the microprocessor-controller 142, which is built into the overall sterilization apparatus in this embodiment.

An embodiment of the present invention employing a cassette for holding, sterilizing, and maintaining in sterile condition articles to be sterilized will now be described. With reference to FIG. 6, for example, the cassette, loaded with articles to be sterilized, is placed into the sterilization chamber 110. A direct, fluid connection from inlet port 135 to an input port in the cassette is made. This direct, fluid connection allows the multicomponent vapor, including sterilant vapor, to flow through the cassette, sterilizing the inside of the cassette and the articles enclosed therein. The sterilant vapor flows out an output port, and into the sterilization chamber 110. If a portion of the flow of multicomponent or sterilant vapor is allowed to flow over the outside of the cassette, it, too, can be sterilized simultaneously. The multicomponent or sterilant vapor then passes through the sensor probe 50 for measurement as described.

Alternatively, the cassette input port may be connected as described above, and the output port be connected in a like manner, to an outlet port such as the outlet port 183 of FIG. 6. However, if such connection were made, the sensor probe would have to be mounted downstream of the sterilization chamber, e.g., as shown in position C of FIG. 2. In this manner, the concentration of hydrogen peroxide flowing out of the cassette would be measured just after its exit from the cassette.

Cassettes as described here are more fully described in copending, commonly assigned U.S. application Ser. No. 08/290,567, filed Aug. 15, 1994, now U.S. Pat. No. 5,470,548, and U.S. application Ser. No. 08/282,228, filed Jul. 29, 1994, now U.S. Pat. No. 5,534,221. The disclosures of these two applications are incorporated herein by reference.

Although the preferred embodiment of the present invention comprises hydrogen peroxide vapor as the sterilant vapor and electromagnetic radiation having wavelengths in the infrared region as the radiation for detecting the sterilant concentration, other wavelengths of electromagnetic radiation may be useable for this or other sterilants. Sterilants other than hydrogen peroxide can be used with the system and method of the present invention. The selection of the proper wavelengths depend on electromagnetic properties of the sterilant vapor and any other vapors present in a multicomponent vapor. Preferably the wavelengths chosen allow the concentration of one component to be determined by a subtraction procedure, as described hereinabove. More preferably, a wavelength of absorbance unique to the sterilant vapor of interest would be available and not interfered with by other components of the multicomponent vapor. This is not the case when the sterilant vapor is derived from an aqueous solution of hydrogen peroxide, and infrared radiation is employed, since the absorbance of hydrogen peroxide is interfered with by the absorbance of water at the same wavelengths. The absorbances must be adjusted accordingly.

The advantages of the preferred embodiment are, inter alia, that the system can measure operational parameters, particularly including the concentration of the sterilant vapor in the sterilization chamber, but also including other highly influential parameters of the sterilization chamber affecting the sterilization, including the temperature, pressure and relative humidity within the sterilization chamber, and the system can then control and optimize each of these operational parameters to achieve the optimum sterilization or decontamination level, in the shortest amount of time, and at the least economic expense.

While the invention has been described herein with reference to the preferred embodiments, it is to be understood that it is not intended to limit the invention to the specific forms disclosed. On the contrary, it is intended to cover all modifications and alternative forms falling within the spirit and scope of the invention.

What is claimed is:

1. A system for maintaining a selected concentration of a sterilant vapor during vapor phase sterilization of articles, the system comprising:

a sterilization chamber fluidly connected to a source of a multicomponent vapor, said multicomponent vapor containing a concentration of a sterilant vapor and a concentration of at least one other vapor;

a radiation source for providing electromagnetic radiation at a plurality of wavelengths, absorption of said radiation at a first of said wavelengths being indicative of a concentration of said multicomponent vapor, and absorption of radiation at a second of said wavelengths being indicative of a concentration of said other vapor of said multicomponent vapor;

a sensor probe providing a path through said multicomponent vapor for said radiation;

a detector for detecting and quantitating said electromagnetic radiation at least at said first and second wavelengths, said detector generating at least first and second absorbance signals corresponding to said first and second wavelengths, said first absorbance signal having a strength proportional to the concentration of said multicomponent vapor and said second absorbance signal having a strength proportional to the concentration of said other vapor;

a microprocessor means for comparing first and second absorbance signals generated with known concentrations of the sterilant vapor and the other vapor to determine an extinction coefficient and for (a) subtracting first and second absorbance signals generated during a sterilization cycle to determine a difference signal, (b) calculating a concentration of the sterilant vapor from the determined extinction coefficient and the difference signal, and (c) generating an output signal that is indicative of the calculated concentration of sterilant vapor;

a controller which receives said output signal and controls addition of said multicomponent vapor to said sterilization chamber to maintain the selected concentration of said sterilant vapor in said chamber.

2. The system as claimed in claim 1, wherein said sterilant vapor is hydrogen peroxide vapor and said at least one other vapor is water.

3. The system as claimed in claim 1, wherein said source of multicomponent vapor is a vaporizer, and said multicomponent vapor is vaporized from an aqueous solution of hydrogen peroxide.

4. The system as claimed in claim 3, wherein said aqueous solution of hydrogen peroxide contains 3 to 98 percent hydrogen peroxide by weight.

5. The system as claimed in claim 3, wherein said aqueous solution of hydrogen peroxide contains 30 to 35 percent hydrogen peroxide by weight.

6. The system as claimed in claim 1, wherein said electromagnetic radiation includes wavelengths in the infrared region.

7. The system as claimed in claim 1, wherein said radiation source comprises fiber optic cables for transmission of said radiation to a portion of said chamber in fluid connection with said multicomponent vapor and then to said detector.

8. The system as claimed in claim 7, wherein said fiber optic cables are attached to said sensor probe to form a single unit disposed within said portion of said chamber.

9. The system as claimed in claim 7, wherein said portion of said chamber comprises walls and said fiber optic cables are attached to said walls.

10. The system of claim 1 for maintaining a selected concentration of sterilant vapor during vapor phase sterilization of articles, wherein said sterilant is hydrogen peroxide vapor and said other vapor is water vapor, wherein said multicomponent vapor is obtained from an aqueous solution of hydrogen peroxide which contains 3% to 98% hydrogen peroxide by weight;

said radiation source being a light source for providing multichromatic light;

said sensor probe being mounted inside the chamber, the sensor probe providing a path for the light through the multicomponent vapor to the detector for detecting and quantitating, said sensor probe further providing a nonlinear path for said light using light reflecting devices within said sensor probe;

and said system further comprising:

fiber optics for connecting the light source to the sensor probe and for connecting the sensor probe to the detector.

11. A system for maintaining a selected concentration of a hydrogen peroxide vapor, the system comprising:

a chamber fluidly connected to a source of a multicomponent vapor, said multicomponent vapor containing at least water vapor and hydrogen peroxide vapor obtained from an aqueous solution of hydrogen peroxide which contains 3 to 98 percent hydrogen peroxide by weight;

a light source for providing multichromatic light, light of a first wavelength being characteristic of an absorption spectra of said multicomponent vapor as a whole, and light of a second wavelength being characteristic of an absorption spectra primarily of said water vapor;

a detector positioned for detecting said light of at least the first and second wavelengths, from the light source which has passed through the multicomponent vapor, said detector generating at least first and second absorbance signals quantizing absorption of light at said first and second wavelengths;

a microprocessor which a) receives said first and second absorbance signals, b) compares at least said first and second absorbance signals with reference absorbance signals generated from known concentrations of hydrogen peroxide vapor and water vapor, c) calculates a hydrogen peroxide vapor concentration from said comparison of said absorbance signals, and d) generates an output signal proportional to said hydrogen peroxide vapor concentration;

a controller which receives said output signal and controls addition of said multicomponent vapor to said chamber to maintain the selected concentration of said hydrogen peroxide vapor in said chamber.

12. The system as claimed in claim 11 further including a sensor probe mounted inside the chamber, the sensor probe providing a path for the light through the multicomponent vapor.

13. The system as claimed in claim 11 further including a sensor probe located within an outlet port to the chamber, the sensor probe providing a path for the light through the multicomponent vapor.

14. A system for maintaining a selected concentration of a hydrogen peroxide vapor during vapor phase sterilization of articles, the system comprising:

a sterilization chamber connected to a source of a multicomponent vapor, said multicomponent vapor containing hydrogen peroxide vapor and water vapor;

a radiation source for providing electromagnetic radiation at a plurality of wavelengths, said radiation at one of said wavelengths being absorbed by said multicomponent vapor as a whole, and radiation at a second of said wavelengths being absorbed by said water vapor of said multicomponent vapor;

a first sensor probe providing a path through said multicomponent vapor for said radiation, the sensor probe comprising a protective shield for preventing interference with said radiation by articles in said chamber and for allowing free access to said radiation by said multicomponent vapor;

a detector for detecting and quantitating the electromagnetic radiation of the multicomponent vapor absorbed wavelength and the water vapor absorbed wavelength which passes through the probe, said detector generating a detector signal indicative of (i) the received electromagnetic radiation of the multicomponent vapor absorbed wavelength and (ii) the received electromagnetic radiation of the water vapor absorbed wavelength;

a microprocessor for a) receiving said detector signal, b) determining a hydrogen peroxide vapor concentration from said detector signal indicative of the received electromagnetic radiation of the multicomponent vapor absorbed wavelength and the received electromagnetic radiation of the water vapor absorbed wavelength and c) generating a first output signal proportional to said hydrogen peroxide vapor concentration;

a second probe disposed in the chamber for sensing at least one of temperature, pressure, and humidity and generating a second output signal indicative thereof;

a controller which receives the first and second output signals for controlling at least one of temperature, pressure, and humidity and addition of said multicomponent vapor to said sterilization chamber to maintain selected conditions in said chamber.

15. A method of vapor phase sterilization comprising:

a) injecting a multicomponent liquid into a vaporizer and forming a multicomponent vapor, said multicomponent vapor including a sterilant vapor and an other vapor;

b) passing said multicomponent vapor to a sterilization chamber;

c) directing a polychromatic beam of electromagnetic radiation through a portion of said chamber, said radiation including a first characteristic wavelength which is characteristically absorbed by both said sterilant vapor and said other vapor and a second characteristic wavelength which is characteristically absorbed primarily by said other vapor;

d) measuring the electromagnetic radiation beam after passing through the multicomponent vapor;

e) determining a relative absorption of the first and second characteristic wavelengths from the measurement of the electromagnetic radiation beam;

f) repeating steps (a)–(e) for each of a plurality of samples with known concentrations of the sterilant vapor and the other vapor and determining a Beer's Law extinction coefficient from the relative absorption of the first and second characteristic wavelengths;

g) repeating steps (a)–(e) for a sample of the multicomponent vapor whose concentrations of the sterilant vapor and the other vapor are to be determined;

h) determining concentrations of at least the sterilant vapor in the sample from the determined relative absorption of the characteristic wavelengths and the extinction coefficient;

i) controlling further injection of said multicomponent liquid to said vaporizer in accordance with the determined concentration to maintain a selected concentration of sterilant vapor in said chamber.

16. The method as claimed in claim 15, wherein said sterilant vapor is hydrogen peroxide vapor.

17. The method as claimed in claim 16, wherein said hydrogen peroxide vapor is obtained from an aqueous solution of hydrogen peroxide which contains 3 to 98 percent hydrogen peroxide by weight.

18. The method as claimed in claim 15, wherein said electromagnetic radiation includes wavelengths in the infrared region.

19. The method as claimed in claim 15, wherein said step of directing includes passing said radiation through fiber optic cables for transmission of said radiation to said chamber and to said detector.

20. The method as claimed in claim 19, wherein said fiber optic cables are attached to said sensor probe to form a single unit disposed within said chamber.

21. The method as claimed in claim 19, wherein said chamber comprises walls and said fiber optic cables are attached to said walls.

22. The method as claimed in claim 15, wherein said step of controlling includes utilizing a microprocessor-controller programmed for controlling at least one parameter within said chamber in addition to the sterilant vapor concentration, said at least one parameter selected from the group consisting of temperature, pressure, and humidity.

23. A method of vapor phase hydrogen peroxide sterilization comprising:

a) injecting an aqueous liquid solution of (i) hydrogen peroxide and (ii) water into a vaporizer and forming a multicomponent vapor of hydrogen peroxide vapor and water vapor, said multicomponent vapor having a first characteristic absorption spectrum, said water vapor having a second characteristic absorption spectrum, and said hydrogen peroxide vapor having a third characteristic absorption spectrum;

b) passing said multicomponent vapor including the hydrogen peroxide vapor and the water vapor to a sterilization chamber;

c) directing a polychromatic beam of infrared radiation through a portion of said chamber, said infrared radiation including at least (i) a first characteristic wavelength of the first characteristic absorption spectrum and (ii) a second characteristic wavelength of the second characteristic absorption spectrum, which second characteristic wavelength is not characteristic of the third characteristic absorption spectrum;

d) measuring the infrared radiation beam after passing through the multicomponent vapor;

e) determining a relative absorption of the first and second characteristic wavelengths from the measurement of the electromagnetic radiation beam;

f) repeating steps (a)–(e) with each of a plurality of known samples of known concentrations of hydrogen peroxide vapor and water vapor to determine the relative absorptions of the first and second characteristic wavelengths corresponding to known concentrations of hydrogen peroxide vapor and water vapor in the known samples;

g) repeating steps (a)–(e) for an unknown sample of the multi-component vapor in the chamber whose concentrations of hydrogen peroxide vapor and water vapor are to be determined;

h) comparing the relative absorption of the first and second characteristic wavelengths of the unknown sample with the relative absorption of the known sample to determine at least a concentration of the hydrogen peroxide vapor of the unknown sample in the chamber;

controlling further injection of said aqueous solution to said vaporizer in accordance with the determined hydrogen peroxide vapor concentration to maintain a selected concentration of hydrogen peroxide vapor in said chamber.

24. The method as claimed in claim 23, wherein said aqueous solution of hydrogen peroxide contains 10 to 50 percent hydrogen peroxide by weight.

25. The method as claimed in claim 23, wherein said aqueous solution of hydrogen peroxide contains 30 to 35 percent hydrogen peroxide by weight.

* * * * *